United States Patent [19]

Kahn

[11] 4,354,497

[45] Oct. 19, 1982

[54] CARDIAC DEPOLARIZATION DETECTION APPARATUS

[75] Inventor: Alan R. Kahn, Golden Valley, Minn.

[73] Assignee: Medtronic, Inc., Minneapolis, Minn.

[21] Appl. No.: 799,258

[22] Filed: May 23, 1977

[51] Int. Cl.³ ............................................. A61N 1/36
[52] U.S. Cl. ............................................. 128/419 D
[58] Field of Search ............... 128/2.06 A, 2.06 B, 128/2.06 G, 2.06 R, 419 D

[56] References Cited

U.S. PATENT DOCUMENTS

| | | | |
|---|---|---|---|
| 3,267,934 | 8/1966 | Thornton | 128/2.06 A |
| 3,438,368 | 4/1969 | Karsh | 128/2.06 A |
| 3,699,946 | 10/1972 | Michel | 128/2.06 A |
| 3,707,959 | 1/1973 | Wilton-Davies | 128/2.06 A |
| 3,937,226 | 2/1976 | Funke | 128/419 D |

*Primary Examiner*—William E. Kamm
*Attorney, Agent, or Firm*—Schroeder, Siegfried, Vidas, Steffey & Arrett

[57] ABSTRACT

Apparatus which detects ventricular depolarizations originating at an ectopic focus. Ventricular depolarization is sensed at a plurality of areas of the heart including one area within the interventricular septum or near the right ventricular apex. Logic circuitry responds to the sensed depolarizations to discriminate between normal and abnormal origination of an impulse propagated through the ventricular conduction system. A signal representative of such abnormal impulse origination may be employed in any desired manner.

7 Claims, 5 Drawing Figures

CARDIAC DEPOLARIZATION DETECTION APPARATUS

BACKGROUND OF THE INVENTION

It is known that a cardiac tachyarrhythmia can be converted to a rhythm that is more physiologically tolerable through the proper application of electrical energy. This process is commonly referred to as cardioversion.

Cardioversion requires the detection of the arrhythmia, or its onset, prior to the application of electrical energy. Within the setting of a modern hospital, this function may be performed with some efficiency. To effect cardioversion in other settings, there have been efforts directed toward the development of an implantable unit to detect and respond appropriately to an arrhythmia. Within an implantable unit, a major difficulty is the determination that cardioversion is necessary.

U.S. Pat. No. 3,805,795 issued Apr. 23, 1974 and entitled Automatic Cardioverting Circuit discloses fully implantable circuitry for detecting the development of a life threatening arrhythmic condition to automatically apply an electrical shock to the heart to restore normal heart activity. The detecting or sensing system of the referenced patent monitors two dynamic characteristics of the heart and defines the absence of both of those characteristics, for a predetermined period of time, as an arrhythmic heart condition. Thus, the device of the referenced patent detects an arrhythmic heart condition only after that condition has developed.

U.S. Pat. No. 3,937,226, issued Feb. 10, 1976 in the name of Herman D. Funke and entitled Arrhythmia Prevention Apparatus, which application is co-owned with the present invention, discusses the disadvantages of cardioversion after development of the arrhythmia. As stated in the Funke application, these disadvantages include higher power requirements and time delays. To overcome these disadvantages, Funke has proposed a system the use of which is intended to prevent the development of fibrillation or other arrhythmias. Essentially, the system senses heart depolarization at a plurality of areas on the heart through a plurality of electrodes connected in spaced relation to the heart. A depolarization occurring at any area on the heart is first sensed by any one of the electrodes and then transmitted to a stimulation device which supplys stimulation pulses to the entire plurality of electrodes connected to the heart. The stimulation thus provided is intended to counter the development of the arrhythmia. However, this system has significant power requirements as a result of its regular application of stimulation energy to the heart.

SUMMARY OF THE INVENTION

The present invention provides apparatus to detect cardiac depolarizations originating from an ectopic focus. Ventricular depolarization is sensed at or across at least two areas of the heart, one such area being within or along the interventricular septum. Said one area may also be near the apex of the right ventricle. A normally conducted impulse will propagate from the interventricular septum (through the His-Purkinje system) to the other ventricular tissue. Thus, a depolarization sensed away from the interventricular septum before a depolarization is sensed along the interventricular septum or near the apex of the right ventricle can be defined as a depolarization originating from an ectopic focus. The present invention provides logic circuitry which responds to the sensed depolarizations to discriminate between the normal and abnormal origination of an impulse propagated through the ventricular conduction system. Following the detection of an impulse propagated from an ectopic focus, an appropriate electrical stimulating signal may be delivered to uniformly depolarize the entire heart muscle and avoid the development of dangerous arrhythmias.

DETAILED DESCRIPTION OF THE DRAWINGS

Figure 1:
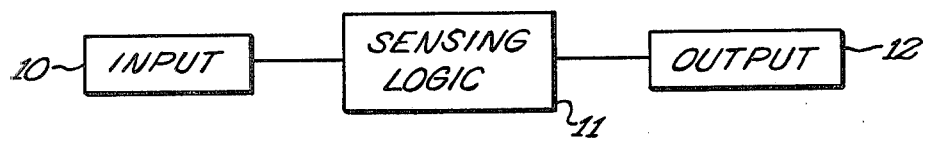
FIG. 1 is a block diagram illustrating the system of the present invention.

FIG. 1 illustrates the operation of the system of the present invention. Input 10 includes an electrode combination adapted to sense a depolarization within the intraventricular septum, sensing near the apex of the right ventricle is adequate, and at least one other electrode combination adapted to sense either an overall ventricular response or a ventricular depolarization at a point more distant from the His bundle than the first electrode combination. In a preferred embodiment, the input 10 includes a plurality of electrode combinations adapted to sense a depolarization of ventricular tissue at a plurality of areas of the heart outside the interventricular septum. Signals indicative of the sensed depolarizations are passed to the sensing logic 11 which detects depolarizations originating from an ectopic focus. On the occurrence of a depolarization which originates from an ectopic focus, sensing logic 11 provides a signal representative of the occurrence of an ectopic beat. The signal from sensing logic 11 is applied to output 12 which responds in any desired manner. For example, output 12 may apply electrical stimulation energy to the heart. The stimulation energy may be in the form of a single stimulation pulse or a burst of programmed pulses without departing from the scope of the present invention, circuitry capable of responding to the initiating signal in any desired manner being known to the prior art. In some instances, the input 10 and output 12 may employ at least some of the same electrodes, depending on the sensing and stimulation requirements of the particular patient. Alternatively, output 12 may indicate the occurrence of a depolarization originating at an ectopic focus, by any suitable signalling device.

As stated above, the input 10 includes an electrode combination adapted to sense a depolarization within the interventricular septum. The signal derived from these electrodes is employed within the sensing logic 11 to detect any impulse propogated through the ventricular tissue originating from an ectopic focus. For example, a depolarization of ventricular tissue resulting from an impulse propogated from an ectopic focus may be sensed at a point adjacent the focus without there being a preceding depolarization within the interventricular septum. Thus, by positioning a plurality of electrode combinations within the ventricular tissue and discriminating between depolarizations which are preceded by a depolarization within the interventricular septum and those which are not, it is possible to detect a depolarization of ventricular tissue resulting from the propogation of an impulse from an ectopic focus. It is presently contemplated that three to ten electrode combinations placed on or adjacent the heart are adequate to detect a depolarization originating from ectopic focus. Also, inasmuch as an impulse may be propogated from an ectopic focus and result in an overall ventricular contraction, it is within the scope of the present invention to sense an overall ventricular contraction, as by skin electrodes, to determine whether that contraction is the result of the normal conduction of an impulse through the ventricular conduction system by establishing whether the contraction was preceded by a depolarization within the interventricular septum. Thus, the present invention contemplates at least one electrode combination adapted to sense a depolarization within the interventricular septum and at least one other electrode combination for sensing either an overall ventricular contraction or a depolarization of ventricular tissue outside the interventricular septum. An electrode combination adapted to sense a depolarization near the apex of the right ventricle is adequate to sense a depolarization within the interventricular septum for the purposes of this invention. The term electrode combination is intended to mean either a pair of electrodes positioned close to each other to sense a depolarization in the region between them, an active electrode positioned at the intended depolarization site and a distant inactive electrode which may be common for other active electrodes or two distant electrodes far apart.

Figure 2:
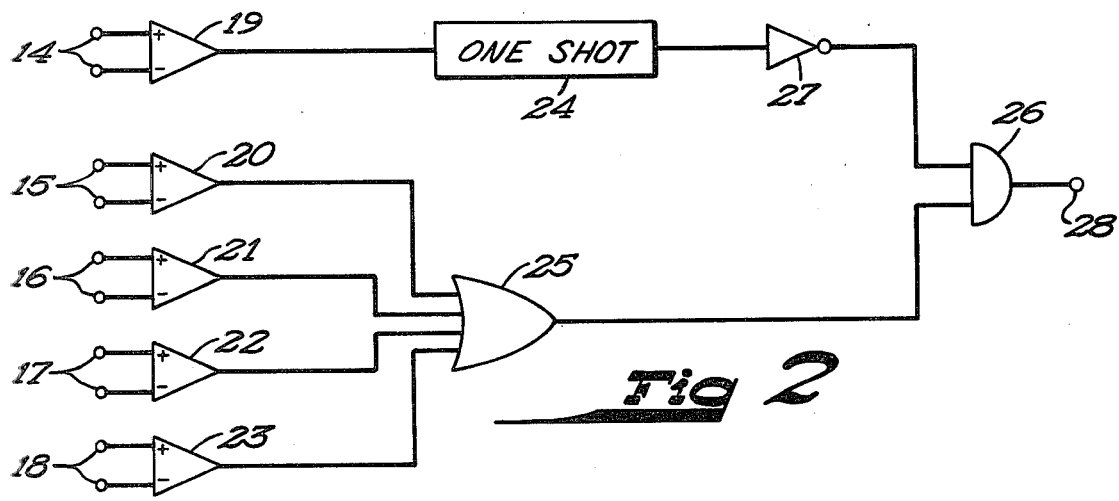
FIG. 2 illustrates a preferred embodiment of a portion of the system of FIG. 1.

Referring now to FIG. 2, there is shown a preferred embodiment of portions of the system in FIG. 1, specifically portions of the input 10 and sensing logic 11. Terminal pairs 14, 15, 16, 17 and 18 are connected, respectively, to a plurality of input signal amplifiers 19, 20, 21, 22 and 23. Input amplifiers 19-23 can be any one of a multiplicity of amplifiers well known to those skilled in the art. The sense output of the amplifier 19 is connected to the input of a one shot 24 while the sense outputs of the amplifiers 20-23 are connected to the inputs of an OR gate 25. The output of the one shot 24 is connected as one input to an AND gate 26, through an invertor 27, and the output of OR gate 25 is connected to the other input of AND gate 26.

The terminals 14 are each adapted for connection to a different electrode of an electrode combination positioned to sense a depolarization within the interventricular septum as by being positioned within the interventricular septum, or near the apex of the right ventricle, for example. Each of the terminal pairs 15-18 are adapted for connection to electrodes positioned to sense depolarization of ventricular tissue at different locations outside the interventricular septum. The electrodes intended for connection to the terminals of like reference numeral are intended to cooperate to sense a depolarization of ventricular tissue and may be positioned within or adjacent to the heart tissue in closer proximity to each other than to electrodes adapted for connection to a terminal having a different reference numeral. Alternatively, amplifiers 20-23 may be connected to a distant, indifferent electrode via one of the terminals 15-18 and different active electrodes associated with different locations, each of these alternative electrode configurations being referred to herein as electrode combinations or electrode pairs.

In operation, a depolarization sensed between an electrode pair will be applied across the terminals to which the electrode pair is connected and be amplified by one of the respective amplifiers 19-23. For example, assuming a signal sensed by an electrode pair is applied across the terminals 15, it will be amplified by amplifier 20 and be presented to one of the inputs of OR gate 25. A signal appearing at one input of OR gate 25 will cause its output to go "high" and present one "high" input to AND gate 26.

The output of one shot 24 is normally "low". Thus, a signal applied across the terminals 15, and not preceded by a signal applied across the terminals 14, will result in two "high" inputs to AND gate 26 and a "high" output from AND gate 26. The output from AND gate 26 is provided to a terminal 28 which is adapted for connection to the output 12 of FIG. 1, the output 12 responding to a "high" signal at terminal 28. A signal appearing across any of the terminal pairs 15-18 without a preceding signal appearing across the terminals 14 will result in a "high" signal at the terminal 28.

A signal appearing across the terminals 14 will trigger the one shot 24 causing its output to go "high" to result in one "low" input to AND gate 26. This "low" at one input of AND gate 26 will maintain the terminal 28 "low" no matter what the state at the other input to AND gate 26, so long as the output of one shot 24 remains "high". The time that one shot 24 remains "high" is set long enough so that the entire heart can be depolarized within that time, but short enough so that another beat cannot begin before the one shot 24 has returned to the "low" state. It is presently contemplated that one shot 24 remain "high" for a period of 120-135 milliseconds following the appearance of a signal across the terminals 14 to effectively prevent an impulse first sensed at the electrode pair connected to the terminals 14 from producing a "high" signal at terminal 28 through the propogation of that impulse and its detection at any of the electrode pairs connected to the terminals 15-18. As described, signals sensed by the electrode pairs connected to the terminals 15-18 may be stated as resulting in an initiate signal to output 12 which is blocked from the terminal 28 on the sensing of a preceding depolarization by the electrode pair connected to the terminals 14.

The embodiment of FIG. 2 operates on the assumption that the "high" period of the one shot 24 can be set to correspond to the period of time that it takes the conducted depolarization signal to travel from the terminal fibers of the bundle of His in the ventricular septum through the heart muscle and past the electrode pairs connected to the terminals 15-18. If the conduction time grows longer, however, it may be that a naturally conducted depolarization could be sensed by one of the more remote electrode pairs 15-18, resulting in a false indication of an ectopic depolarization. On the other hand, if the one shot time period is extended with a safety margin to account for this possibility, real ectopic depolarizations falling within the time period may not be detected.

Figure 3:
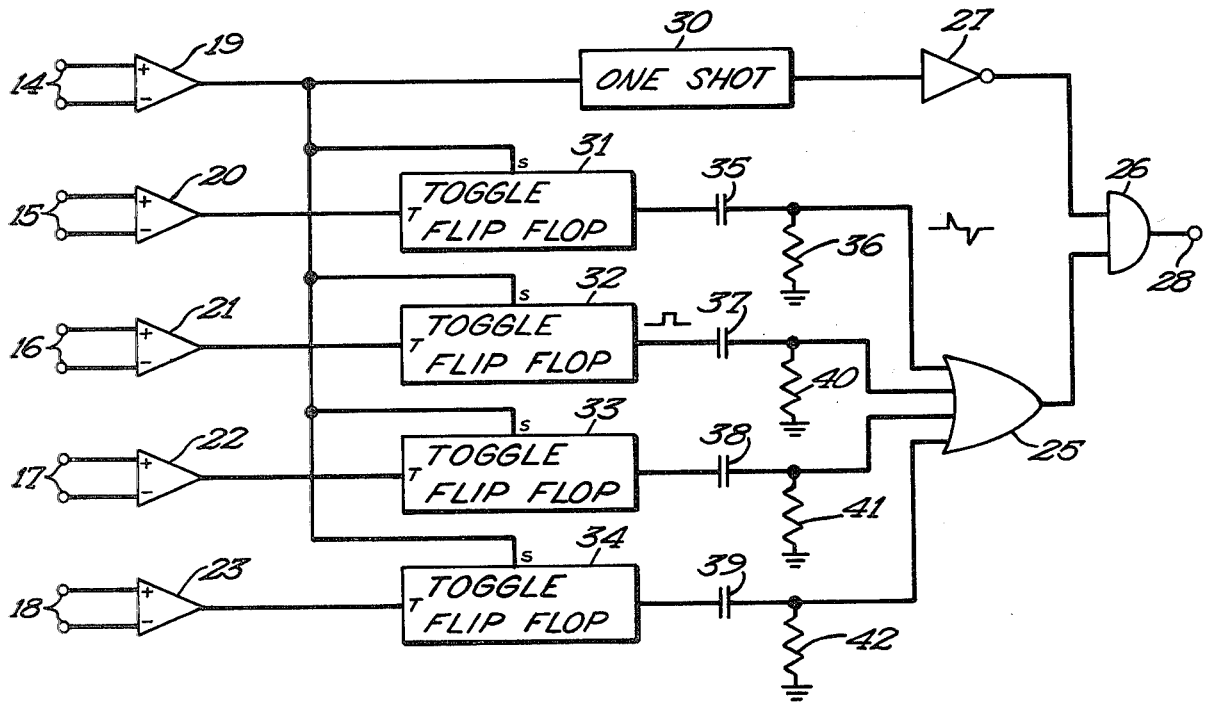
FIG. 3 illustrates another preferred embodiment of a portion of the system of FIG. 1.

Referring now to FIG. 3, there is shown another preferred embodiment of a portion of the system of FIG. 1. In FIG. 3, and throughout the drawings, like reference numerals designate functionally similar or identical elements. Thus, terminals 14 are adapted for connection to an electrode pair positioned to sense a depolarization within the interventricular septum, as by sensing a depolarization near the right ventricular apex, while terminals 15-18 are adapted for connection to electrode pairs placed to sense depolarization within ventricular tissue outside the interventricular septum, the terminals 14-18 being again connected to sense amplifiers 19-23. The embodiment of FIG. 3 is intended to operate in a manner that avoids the possibility of generating a false indication of an ectopic depolarization or missing real ectopic depolarizations.

In FIG. 3, the output of sense amplifier 19 is connected as an input to one shot 30 and to the set terminal of toggle flip flops 31, 32, 33 and 34. The output of sense amplifiers 20, 21, 22 and 23 are connected, respectively, to the input of toggle flip flops 31, 32, 33 and 34. The output of toggle flip flop 31 is connected to one input of OR gate 25 through a positive edge trigger formed of capacitor 35 and resistor 36. Similarly, toggle flip flops 32-34 have their outputs connected to different inputs of OR gate 25 through positive edge triggers formed of capacitors 37-39 and resistors 40-42. The output of OR gate 25 is connected as an input to AND gate 26 and the output of one shot 30 is connected as the other input to AND gate 26 through inverter 27.

Toggle flip flops 31-34 are of the type whose output goes "high" on the occurrence of a "high" signal at their set terminals and alter the state of their output between "high" and "low" on the occurrence of each signal at their input (T). Thus, on the sensing of a depolarization adjacent to the interventricular septum, amplifier 19 will produce a signal to set each of the toggle flip flops 31-34 causing their outputs to go "high" as illustrated at the output of the flip flop 31. The setting of the toggle flip flops 31-34 will result in a spike appearing at each of the inputs of OR gate 25 (one illustrated) resulting in a short duration "high" output from OR gate 25 which appears as an input to AND gate 26.

The output of one shot 30 is normally "low" and is triggered to its "high" state on the occurrence of the signal which sets the flip flops 31-34. When the output of one shot 30 goes "high" it is inverted by inverter 27 resulting in a "low" input to AND gate 26 to block from the terminal 28 that "high" output signal of OR gate 25 which results from the setting of the toggle flip flops 31-34. It is contemplated that one shot 30 will remain "high" for a period of 2-5 milliseconds after being triggered which is sufficient to block the signal resulting from the setting of the toggle flip flops 31-34 from the terminal 28.

Following the sensing of a depolarization adjacent the interventricular septum, the impulse producing that depolarization will be propogated through the ventricular conduction system resulting in a depolarization at each of the electrode pairs connected to the terminals 15-18. With the sensing of these depolarizations, each of the amplifiers 20-23 will provide an input signal to the respective flip flops 31-34 causing the flip flops 31-34 to "toggle" resulting in a "low" output from flip-flops 31-34.

In this state, any subsequent ectopic depolarization not associated with the propagated depolarization and sensed by an electrode pair connected to any of the terminals 15-18 will result in another input to the associated flip flop causing its output to "toggle" "high" producing a "high" spike input to OR gate 25 and AND gate 26. One shot 30 is not triggered by this subsequent sensed depolarization, so its output remains "low" and is inverted to appear as another "high" input to AND gate 26 thus allowing the "high" signal from OR gate 25 to pass to terminal 28 as an initiate signal for output 12. Thus, the operation of the FIG. 3 embodiment relates to the sequence of detection of conducted and ectopic depolarizations to distinguish between the two, and is relatively independent of the expected time period of a conducted depolarization.

From the above, it is apparent that the present invention provides a system by which a depolarization of ventricular tissue which is not preceded by a depolarization within or along the interventricular septum can be detected and discriminated from a depolarization which is preceded by a depolarization within or along the interventricular septum. Thus, the system of the present invention effectively detects depolarizations of ventricular tissue which originate from an ectopic focus and provides an output signal on the occurrence of such depolarizations. Stated another way, the present invention discriminates between impulses which are conducted normally through the ventricular conduction system (i.e., those which pass first through the interventricular septum) and those which result from the propagation of an impulse having an ectopic focus. The electrodes employed within the system of the present invention may take any form known to the prior art, and may be positioned within or on the tissue or in any other operative relationship to the tissue in accordance with the design of the electrode in question. For example, and as discussed below, it is presently contemplated that the well known bipolar, transvenous lead electrode is adequate for use within the system of the present invention to sense depolarization within the interventricular system. Further, while the selection of the output 12 is within the skill of those familiar with the art, it is suggested that the output 12 have either sufficient refractory or "on" time such that its operation is not reinitiated by a depolarization resulting from its output or any other depolarization, normal or otherwise, resulting from the propagation of an already sensed impulse.

Figure 4:
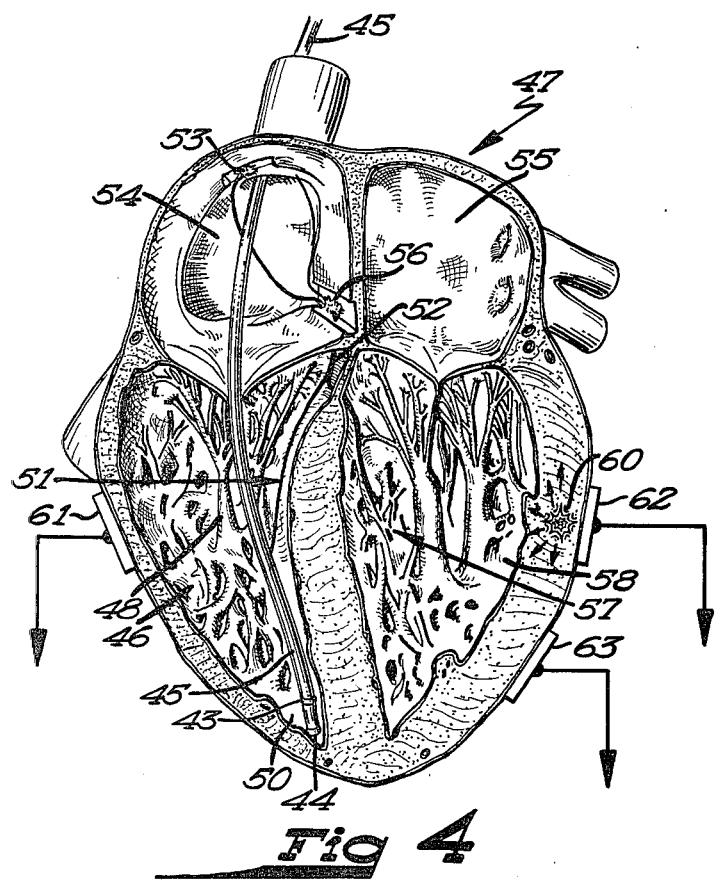
FIG. 4 depicts a view of the chambers of the heart and lead placements suitable for practicing the present invention.

Referring now to FIG. 4, there is depicted the placement of a first pair of distal electrodes 43, 44 on a lead 45 of a conventional design well known in the art in the right ventricle 46 of the heart 47. The distal electrode 44 is lodged under fluoroscopy into the trabeculae 48 of the right ventricle near the apex 50 in a manner well known in the art. This interior surface position of contact is adjacent to the first muscle cells to be depolarized by a signal travelling down the right bundle branch 51 of the bundle of His, the heart's electrical conduction system. For an explanation of the heart's conductive system, see, for example, "The Heart's Pacemaker" by E. F. Adolph, *Scientific American*, Vol. 216, No. 3, pp. 32-37, March 1967.

Briefly stated, the rhythmic contraction of the heart is accomplished by propagation of an electrical depolarization signal periodically originating at the sinus node 53 through the walls of the right atrium to the atrio-ventricular node 56. Coincidentally, the right and left atria contract. The signal is then transmitted through the bundle of His 52 to the right and left bundle branches 51 and 57, respectively, and through the muscle of the respective right and left ventricles 46 and 58. Thus, the ventricles contract shortly after (on the order of 100-200 milliseconds) and in rhythm with the atria.

As the electrical signal travels down the right bundle branch 51, and reaches the myocardial cells near the apex, they depolarize, and the wave of electrical depolarization is sensed across the electrodes 43 and 44. A high output spike may be sensed as the cells immediately in contact with the electrode 44 depolarize. The sensed signal is, however, a composite signal of the depolarizations over time occurring both before and after the sensed spike. The depolarization wave travels to the far reaches of the ventricular muscle about 80 milliseconds after it reaches the bundle of His.

A depolarization occurring spontaneously in myocardial cells other than the sinus node 53 or the atrio-ventricular node 56 is referred to as an ectopic focus. When such an ectopic depolarization occurs, as at an ectopic focus as depicted at 60 in the wall of the left ventricle 58 in FIG. 4, a depolarization wave expands outward in all directions from the focus, travelling, however, more rapidly on the cells of the conductive system than through myocardial muscle cells. Once depolarized, a myocardial cell must re-establish its electrical charge over a period of time, and, consequently, is vulnerable to a subsequent, closely timed depolarization. Thus, ectopic and normal depolarizations may interfere with one another and may induce a dangerous arrhythmia in the heart.

The invention as hereinbefore described recognizes that ectopic depolarizations may be distinguished from normal depolarizations by the order in which signals are picked up on electrodes close to the bundle of His and those electrodes remote from the bundle of His. As illustrated in FIG. 4, the disposition of the remote electrodes may be around the periphery of the heart. For example, the electrodes may comprise a remote indifferent plate electrode 61 and one or more electrodes 62, 63, of any suitable configuration on the opposite side of the heart from the indifferent electrode. Such active electrodes each form an electrode pair with the inactive or indifferent electrode 61 and may take the form of the onlay epicardial pacemaker lead disclosed, for example, in the article entitled "Electrophysiology of the Onlay Epicardial Pacemaker Lead in the Postoperative Period. An Experimental Study", by N. P. D. Smyth, et al., in *Medical Instrumentation*, Vol. 7, No. 3, pp. 180-184, May-August 1973.

Hence, in FIG. 4, if an ectopic focus remote from electrodes 43, 44 (e.g., focus 60— fires, the waveform picked up across electrodes 61 and 62 or 63 will precede that picked up across electrodes 43 and 44. The sensing logic and input circuitry hereinbefore disclosed can thus cooperate with electrodes 43, 44, 61, 62 and 63 to distinguish an ectopic beat from a regular heart beat.

Figure 5:
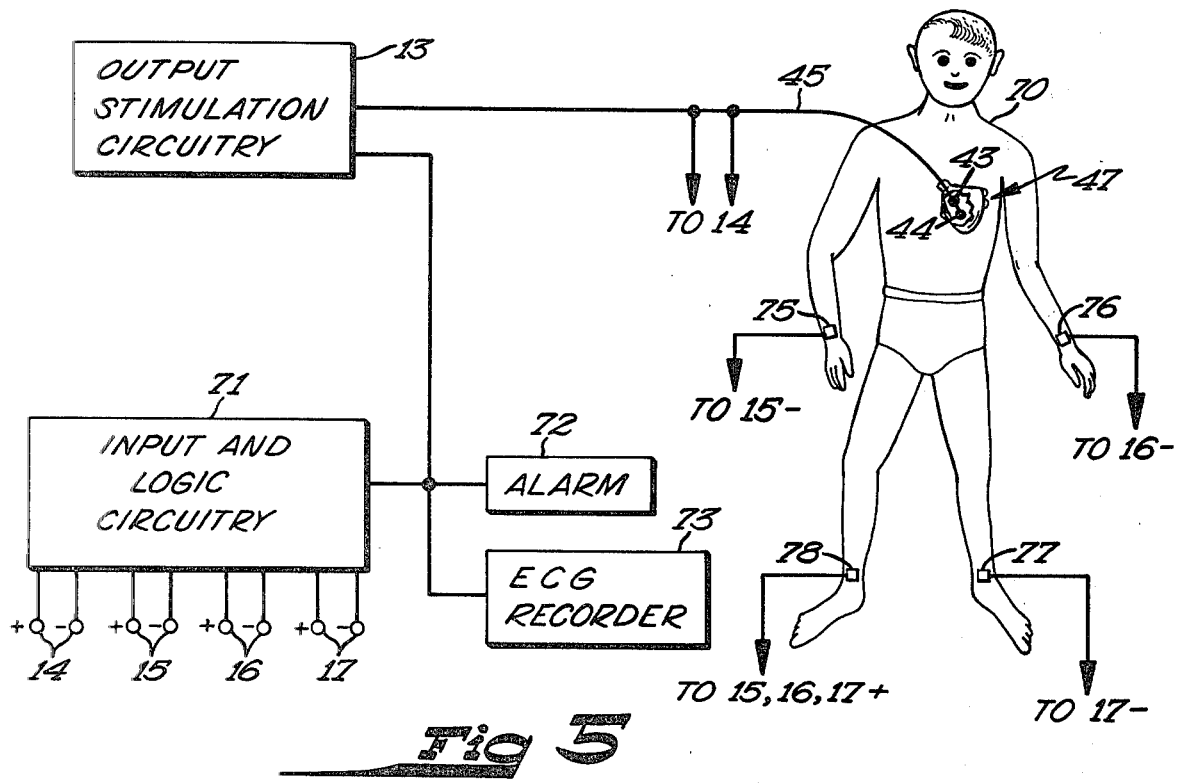
FIG. 5 depicts a system for monitoring, recording and sounding an alarm and pacing a patient's heart in accordance with the present invention.

Turning now to FIG. 5, there is depicted a system for monitoring a patient's heart, recording the patient's ECG, and initiating artificial pacing to counter arrhythmias. The patient 70 wears active arm and leg electrodes 75, 76 and 77 and inactive leg electrode 78 connected to the input terminals 15-17 of an input and logic circuit 71. Input and logic circuit 71 may be one of the circuits of either FIGS. 2 or 3 with the terminals 18 and their associated circuitry eliminated and electrodes 43 and 44 connected to terminals 14. In the manner hereinbefore described, with reference to either of FIG. 2 or 3, the logic portion of input and logic circuit 71 distinguishes ectopic from conducted heart depolarizations and produces an output signal that may trigger the operation of an alarm 72, an electrocardiographic recorder 73 and the appropriate output stimulation circuitry 13 to stimulate the patient's heart. In this manner, the invention is applicable also to an external system useful in maintaining a patient in a hospital room setting.

Many modifications and variations are possible in light of the above teachings. An example of such a modification is the employment of a single electrode pair within the interventricular septum and other means by which an overall ventricular contraction is sensed, as described above. For example, the embodiment of FIG. 3 may be modified so as to use only terminals 14 and 15, terminals 14 adapted for connection to electrodes within or along the interventricular septum. The output of toggle flip flop 31 may be connected through the positive edge trigger, formed by capacitor 35 and resistor 36, directly to one input of AND gate 26 with the other input of AND gate 26 being connected to the output of one shot 30 through inverter 27. OR gate 25 may be eliminated as may flip flops 32-34, and their associated circuitry. In this mode, the terminals 15 may be connected to electrodes adapted for connection to the skin, for example, to sense an overall ventricular contraction, the operation of the remaining circuitry being as described with reference to FIG. 3 with the sensing logic in this instance establishing whether or not the contraction is the result of an impulse propagated through the ventricular conduction system from the interventricular septum. Further, although the present invention has been discussed in terms of ventricular depolarizations, it may be practiced to detect ectopic depolarizations of other than ventricular tissue by placement of electrodes to detect depolarization of a location where it may be first expected to occur (nodes 53 or 56 of FIG. 4, for example) and at other locations where a depolarization may be later expected. It is, therefore to be understood that, within the scope of the appended claims, the invention may be practiced otherwise than is specifically described.

What is claimed is:

1. Cardiac ectopic heat detection apparatus which comprises:
    means for sensing cardiac depolarization including first means for sensing depolarization of a first area of cardiac tissue and second means for sensing depolarization of at least one other area of cardiac tissue, said first area being an area of earlier activation within the ventricular conduction system than any of said other areas;
    output means; and
    means interconnecting said output means and sensing means for providing a signal to said output means only following the occurrence of cardiac depolarization sensed by said second means and not preceded by a depolarization sensed by said first means.

2. The apparatus of claim 1 wherein said interconnecting means comprises:
    third means for responding to the sensing of depolarization by any of said second means to provide a signal to said output means; and
    fourth means responsive to said first means for blocking said signal from said output means for a predetermined period of time following the sensing of depolarization by said first means.

3. The apparatus of claim 2 wherein said third means comprises OR logic means and said fourth means comprises AND logic means.

4. The apparatus of claim 1 wherein said interconnecting means comprises dual state means settable to an initial state in response to the sensing of depolarization by said first means and alterable in state in response to the sensing of depolarization by said second means.

5. In cardiac apparatus of the type having first means for sensing depolarizations resulting from propagation of an impulse at a plurality of areas on a heart and second means for providing signals in response to depolarizations sensed by said first means, the improvement which comprises third means responsive to a normally conducted impulse for rendering said second means nonresponsive to depolarizations sensed by said first means resulting from propagation of said normally conducted impulse, said third means comprising means for detecting depolarizations within or near the interventricular septum and logic means responsive to the sequence of said first means and depolarizations detected within or near the interventricular septum for discriminating between depolarizations resulting from propagation of a normally conducted impulse and those originating from an ectopic focus, said logic means comprising OR logic means for responding to the sensing of depolarization by any of said first means to provide a signal, said second means being responsive to said signal; and AND logic means responsive to sensed depolarizations within or near the interventricular septum for blocking said signal from said second means for a predetermined period of time following a sensed depolarization within or near the interventricular septum.

6. In cardiac apparatus of the type having first means for sensing depolarizations resulting from propagation of an impulse at a plurality of areas on a heart and second means for providing signals in response to depolarizations sensed by said first means, the improvement which comprises third means responsive to a normally conducted impulse for rendering said second means nonresponsive to depolarizations sensed by said first means resulting from propagation of said normally conducted impulse, said third means comprising means for detecting depolarizations within or near the interventricular septum and logic means responsive to the sequence of said first means and depolarizations detected within or near the interventricular septum for discriminating between depolarizations resulting from propagation of a normally conducted impulse and those originating from an ectopic focus, said logic means comprising dual state means settable to an initial state in response to the sensing of depolarizations within or near the interventricular septum and alterable in state in response to the sensing of depolarization by said first means, a different dual state means being asociated with each of said areas on a heart, said logic means further comprising means for responding to each of said dual state means to provide a signal when any of said dual state means are in the intial state, said second means being responsive to said signal, and means for blocking said signal from said second means for a predetermined period of time following a sensed depolarization within or near the interventricular septum.

7. The apparatus of claim 6 wherein the means to provide a signal comprises OR logic means and said blocking means comprises AND logic means.

* * * * *

UNITED STATES PATENT AND TRADEMARK OFFICE
CERTIFICATE OF CORRECTION

PATENT NO. : 4,354,497       Page 1 of 2
DATED : October 19, 1982
INVENTOR(S) : Alan R. Kahn It is certified that error appears in the above-identified patent and that said Letters Patent are hereby corrected as shown below:

Column 8, line 40, after "sensing", insert --the propagation of a--.

Column 8, line 40, after "depolarization", insert --wave--.

Column 8, line 50, delete the words "only" and "occurrence".

Column 8, line 50, after "the", insert --sensing--.

Column 8, line 50, after "of", insert --a--.

Column 8, line 51, delete the words "sensed" and "and".

Column 8, line 51, before "not", insert --that is--.

Column 8, line 51, after "depolarization", insert --wave--.

Column 8, line 52, delete the words "a" and "sensed".

Column 8, line 52, before "depolarization", insert --the sensing of said cardiac--.

UNITED STATES PATENT AND TRADEMARK OFFICE
CERTIFICATE OF CORRECTION

PATENT NO. : 4,354,497

DATED : October 19, 1982

INVENTOR(S) : Alan R. Kahn

It is certified that error appears in the above-identified patent and that said Letters Patent are hereby corrected as shown below:

Column 8, line 52, after "depolarization", insert --wave--.

Signed and Sealed this

Fifth Day of July 1983

[SEAL]

Attest:

GERALD J. MOSSINGHOFF

Attesting Officer

Commissioner of Patents and Trademarks